United States Patent
Glavin et al.

(10) Patent No.: US 12,429,445 B2
(45) Date of Patent: Sep. 30, 2025

(54) REAL-TIME IMPEDANCE SPECTROSCOPY USING 2D TRANSITION METAL DICHALCOGENIDE MATERIAL-BASED CHEMICAL SENSOR SYSTEMS

(71) Applicant: Government of the United States, as represented by the Secretary of the Air Force, Wright-Patterson AFB, OH (US)

(72) Inventors: Nicholas R. Glavin, Springboro, OH (US); David C. Moore, Sellersburg, IN (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 257 days.

(21) Appl. No.: 18/110,998

(22) Filed: Feb. 17, 2023

(65) Prior Publication Data
US 2023/0296544 A1     Sep. 21, 2023

Related U.S. Application Data

(60) Provisional application No. 63/321,805, filed on Mar. 21, 2022.

(51) Int. Cl.
*G01N 27/02*     (2006.01)

(52) U.S. Cl.
CPC ......... *G01N 27/026* (2013.01); *G01N 27/021* (2013.01); *G01N 27/028* (2013.01)

(58) Field of Classification Search
CPC .... G01N 27/26; G01N 27/021; G01N 27/028; G01N 27/127; G01N 33/0036; G01N 2027/222

(Continued)

(56) References Cited

U.S. PATENT DOCUMENTS

| | | | |
|---|---|---|---|
| 2011/0197657 A1* | 8/2011 | Gole | G01N 27/127 438/49 |
| 2014/0273259 A1* | 9/2014 | Friedman | B82Y 15/00 436/112 |

(Continued)

OTHER PUBLICATIONS

Kumar, S.; Pavelyev, V.; Mishra, P.; Tripathi, N.; Sharma, P.; Calle, F.; A review on 2D transition metal di-chalcogenides and metal oxide nanostructures based NO2 gas sensors. Materials Science in Semiconductor Processing, 2019, 107, 104865, 1-23.

(Continued)

*Primary Examiner* — Christopher P McAndrew
(74) *Attorney, Agent, or Firm* — AFMCLO/JAZ; Jeffrey V. Bamber; James F. McBride (57) ABSTRACT

The present invention relates to real-time impedance spectroscopy using 2d transition metal dichalcogenide material-based chemical sensor systems and methods of making and using same. Impedance approach to breakdown the resistance into multiple, measureable resistance components is used in such system. Thus, a real time impedance can be used to measure the resistance of a flake network when exposed to a gas. This change in the resistance can now be used to determine the concentration of a gas of interest, in many cases, down to a parts per trillion level. Thus, gas concentrations can efficiently and effectively determined on a more accurate level and less expensively than before.

20 Claims, 10 Drawing Sheets

(58) Field of Classification Search
USPC .......................................................... 324/693
See application file for complete search history.

(56) References Cited

U.S. PATENT DOCUMENTS

| | | | | |
|---|---|---|---|---|
| 2015/0260706 | A1* | 9/2015 | Killard | A61B 5/097 436/113 |
| 2021/0341406 | A1* | 11/2021 | Yao | G01N 27/127 |
| 2022/0042941 | A1* | 2/2022 | Sakhuja | G01N 27/127 |

OTHER PUBLICATIONS

Yang, S., Jiang, C., & Wei, S. Huai; Gas sensing in 2D materials. In Applied Physics Reviews 2017, 4, 2, 1-36.

Meng, Z.; Stolz, R. M.; Mendecki, L.; Mirica, K. A.; Electrically-Transduced Chemical Sensors Based on Two-Dimensional Nanomaterials. Chem. Rev. 2019, 119, 478-598.

Yi, N.; Cheng, Z.; Li, H.; Yang, L.; Zhu, J.; Zheng, X.; Chen, Y.; Liu, Z.; Zhu, H.; Cheng, H; Stretchable, ultrasensitive, and low-temperature NO2 sensors based on MoS2@rGO nanocomposites. Materials Today Physics, 2020, 15(2), 100265, 1-13.

Mayorga-Martinez C. C.; Sofer, Z.; Pumera, M.; Layered Black Phosphorus as a Selective Vapor Sensor. Angewandte Chemie—International Edition, 2015, 54(48), 14317-14320.

Tsuyoshi Sakai, Satoko Takase, Y. S.; An Impedancemetric Micro NO2 Sensor Using Oxide and Solid-Electrolyte Thin-Films. 2020, 140(11), 305-308.

Martin, L. Y.; Glass, L. P.; Wang, R. S.; Yong, W.; Gorte, S.; Murray, R. J.; Novack, E. P.; Visser, R. F.; Effect of Electrode Composition and Microstructure on Impendancemetric nitric oxide sensors based on YSZ Electrolyte. Journal of the Electrochemical Society, 2008, 155(1), 32-40.

Cho, H. C.; Takase, S.; Song, J.-H.; Shimizu, Y.; Sensing behavior of solid-state impedancemetric NOx sensor using solid electrolyte transducer and oxide receptor. Sensors and Actuators B, 2013, 187, 94-98.

* cited by examiner

FIG. 8B

REAL-TIME IMPEDANCE SPECTROSCOPY USING 2D TRANSITION METAL DICHALCOGENIDE MATERIAL-BASED CHEMICAL SENSOR SYSTEMS

CROSS-REFERENCE TO RELATED APPLICATION

The present application claims priority to U.S. Provisional Application Ser. No. 63/321,805 filed Mar. 21, 2022, the contents of both such priority documents being hereby incorporated by reference in their entry.

RIGHTS OF THE GOVERNMENT

The invention described herein may be manufactured and used by or for the Government of the United States for all governmental purposes without the payment of any royalty.

FIELD OF THE INVENTION

The present invention relates to real-time impedance spectroscopy using 2D transition metal dichalcogenide material-based chemical sensor systems and methods of making and using same.

BACKGROUND OF THE INVENTION

Current sensor systems used to detect the level of gases are not as sensitive as desired they are typically limited to a gas ppm level for organic gases and inorganic gases including $NO_2$, $CO_2$, $NH_3$, $H_2O$, NO, isopropyl alcohol, methanol, ethanol, aniline, toluene, and napthalene. While certain sensors may be able to achieve a gas ppb sensitivity, the materials and equipment needed to implement such sensor systems are complex, expensive and time consuming to fabricate. Many of the gases that OSHA regulates must be detected and measured at low ppms. However, for practical use, a sensor system needs to be capable of detecting and measuring such gases at several orders of magnitude below such ppm levels. Thus, what is needed is an inexpensive, easy fabricate and use gas detection system.

Applicants recognized that the initial resistance of current flake material networks was too high for effective operation in a gas detection system. Such recognition led Applicants to develop an impedance approach to breakdown the resistance into multiple, measureable resistance components. Thus, a real time impedance can be used to measure the resistance of a flake network when exposed to a gas. This change in the resistance can now be used to determine the concentration of a gas of interest, in many cases, down to a parts per trillion level. Thus, gas concentrations can efficiently and effectively determined on a more accurate level and less expensively than before.

SUMMARY OF THE INVENTION

The present invention relates to real-time impedance spectroscopy using 2D transition metal dichalcogenide material-based chemical sensor systems and methods of making and using same. Impedance approach to breakdown the resistance into multiple, measureable resistance components is used in such system. Thus, a real time impedance can be used to measure the resistance of a flake network when exposed to a gas. This change in the resistance can now be used to determine the concentration of a gas of interest, in many cases, down to a parts per trillion level. Thus, gas concentrations can efficiently and effectively determined on a more accurate level and less expensively than before.

Additional objects, advantages, and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Definitions

Unless specifically stated otherwise, as used herein, the terms "a", "an" and "the" mean "at least one".

As used herein, the terms "include", "includes" and "including" are meant to be non-limiting.

As used herein, the words "about," "approximately," or the like, when accompanying a numerical value, are to be construed as indicating a deviation as would be appreciated by one of ordinary skill in the art to operate satisfactorily for an intended purpose.

As used herein, the words "and/or" means, when referring to embodiments (for example an embodiment having elements A and/or B) that the embodiment may have element A alone, element B alone, or elements A and B taken together.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Sensor Systems

For purposes of this specification, headings are not considered paragraphs and thus this paragraph is paragraph thirty-six of the present specification. The individual number of each paragraph above and below this paragraph can be determined by reference to this paragraph's number. In this paragraph thirty-six, Applicants disclose a sensor system comprising:
a) substrate comprising a host material having a top side and a bottom, said substrate comprising:
   (i) a layer on the top side of said host material and/or on said bottom side of said host material, said layer comprising a plurality of transition metal dichalcogenide nanoflakes and having a topside and a bottom side;
   (ii) a patterned electrical conductive material being disposed on the topside of said layer, between said substrate and said layer or disposed on the topside of said layer and between said host material and said layer;
b) a power source; preferably said power source is a variable AC frequency power source or a single AC frequency power source, preferably said single AC frequency power source comprises a frequency converter, preferably said frequency converter is a transformer;
   (i) preferably said variable AC frequency power source is selected from the group consisting of a lockin amplifier, a function generator, variable frequency generator, or a potentiostat
   (ii) preferably said single AC frequency power source is selected from the group consisting of a microcontroller, oscillator or inverter circuitry;
c) an alternating current detector comprising a processor for converting alternating current readings into gas concentration, preferably said alternating current detector comprising a processor for converting alternating current readings into gas concentration is a lockin amplifier, an ac voltmeter, an ammeter, a multimeter, a potentiostat, or an integrating circuit; more said alternating current detector comprising a processor for converting alternating current readings into gas concentration is selected from the group consisting of a lockin amplifier or a potentiostat; and
d) an optional gas chamber, when said optional gas chamber is present, said substrate is contained within said optional gas chamber;
said patterned electrical conductive material and one or more of said plurality transition metal dichalcogenide nanoflakes being in electrical communication with said power source and said alternating current detector.

Applicants disclose a sensor system according to paragraph thirty-six wherein:
a) said host material is selected from the group consisting of silicon, silicon dioxide, sapphire, glass, a polymer and mixtures thereof, preferably said polymer is selected from the group consisting of polyethylene naphthalate, polyimide, polycarbonate, and mixtures thereof;
b) said plurality transition metal dichalcogenide nanoflakes comprise $MoS_2$, $WS_2$, $MoSe_2$, $WSe_2$, $MoTe_2$, $WTe_2$ and mixtures thereof;
c) said patterned electrical conductive material comprises a material selected from the group consisting of poly (3,4-ethylenedioxythiophene), poly(3,4-ethylenedioxythiophene) polystyrene sulfonate, poly(pyrrole), polycarbazoles, polyindoles, polyazepines, Cr, Mo, Ti, Sc, Ni, V, Hf, W, Nb, Au, Ag, Cu, Pt and mixtures thereof; more preferably said patterned electrical conductive material comprises a metal selected from the group consisting of Cr, Mo, Ti, Sc, Ni, V, Hf, W, Nb, Au, Ag, Cu, and Pt and mixtures thereof, more preferably said patterned electrical conductive material comprises a metal selected from the group consisting of Mo, Cr, Ti, Au and mixtures thereof, most preferably said patterned electrical conductive material comprises:
   (i) a coating of Mo,
   (ii) a coating of Cr and a coating of Au over said coating of Cr; or
   (ii) a coating of Ti and a coating of Au over said coating of Ti.

Applicants disclose a sensor system according to paragraphs thirty-six through thirty-seven wherein said plurality transition metal dichalcogenide nanoflakes have thickness of from about 0.3 nm to about 10,000 nm, preferably said plurality transition metal dichalcogenide nanoflakes have thickness of from about 1 nm to about 1000 nm, more preferably said plurality transition metal dichalcogenide nanoflakes have thickness of from about 3 nm to about 100.

Suitable transition metal dichalcogenide (TMD) nanoflakes comprising of a transition metal and sulfur, selenium, or tellurium can be obtained from Millipore Sigma (400 Summit Drive, Burlington, MA 01803 USA)

Method of Using Sensor Systems

For purposes of this specification, headings are not considered paragraphs and thus this paragraph is paragraph forty of the present specification. The individual number of each paragraph above and below this paragraph can be determined by reference to this paragraph's number. In this paragraph forty, Applicants disclose a method of determining a gas concentration comprising:
 a) exposing a sensor according to paragraphs thirty-six through thirty-nine to a gas;
 b) taking an electrical signal that is generated by said sensor due to said gas exposure and comparing said electrical signal to a baseline electrical signal; and
 c) generating a gas concentration from said comparison of said electrical signal that is generated by said sensor due to said gas exposure and comparing said electrical signal to a baseline electrical signal.

Applicants disclose a method according to paragraph forty wherein said gas is selected from the group consisting of organic gases, inorganic gases and mixtures thereof, preferably said gas is selected from the group consisting of Water, Ammonia, Benzyl chloride, Carbon monoxide, Carbon dioxide, Carbon disulfide, 1,4-dioxane, Hydrogen sulfide, Chlorine, Chlorine dioxide, Ethylene oxide, Formaldehyde, Hydrogen cyanide, Hydrogen sulfide, Methyl mercaptan, Methacrolein, Acrolein, Diisopropylamine, Tripropylamine, Napthanlene, Nitric oxide, Nitrogen dioxide, Oxygen, Phosphine, Sulfur dioxide, Isopropyl Alcohol, Methanol, Ethanol, Anile and Toluene and mixtures thereof, more preferably said gas is selected from the group consisting of Water, Ammonia, Carbon dioxide, Carbon disulfide, Chlorine, Methacrolein, Acrolein, Napthanlene, Nitric oxide, Nitrogen dioxide, Oxygen, Sulfur dioxide, Isopropyl Alcohol, Methanol, Ethanol and mixtures thereof, most preferably said gas is selected from the group consisting of Water, Ammonia, Carbon dioxide, Napthanlene, Nitric oxide, Nitrogen dioxide, Isopropyl Alcohol, Methanol, Ethanol and mixtures thereof.

Applicants disclose the method of Paragraphs forty through forty-one wherein said gas concentration is from about 1 part per trillion (ppt) to about a million parts per million, preferably said gas concentration is from about 50 ppt to about 100,000 ppm, more preferably said gas concentration is from about 100 ppt to about 10,000, most preferably said gas concentration is from about 1 ppb to about 1000 ppm.

Examples

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Figure 1A:
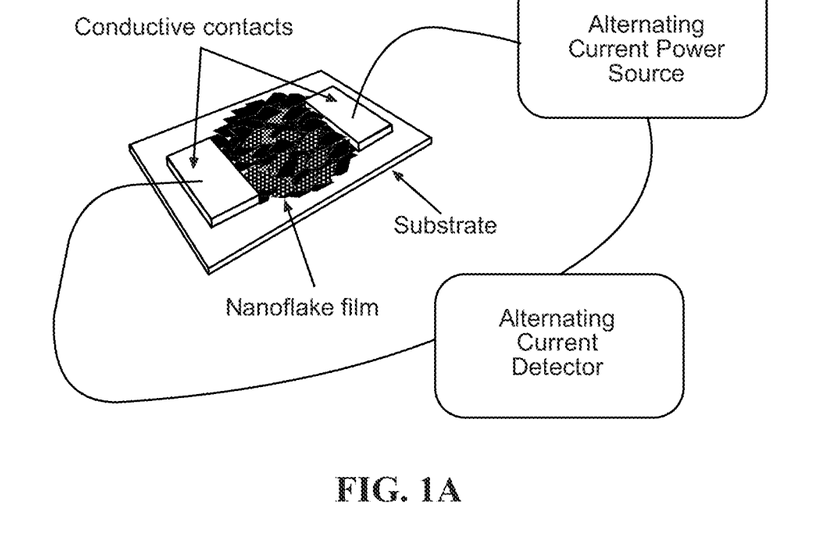
FIG. 1A is a diagram depicting a sensor device coupled to an alternating current power source and an alternating current detector
Figure 1B:
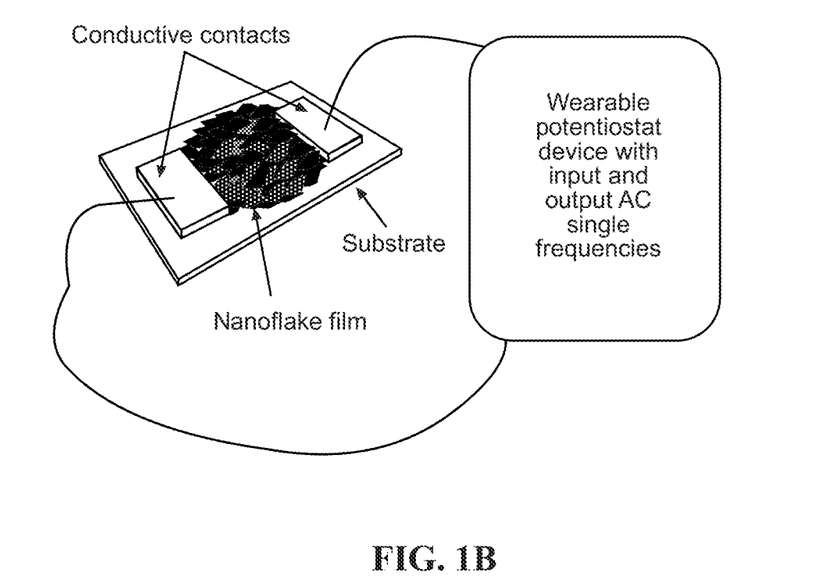
FIG. 1B is a diagram depicting a sensor device coupled to a wearable potentiostat for a gas sensor that can be used on a flexible device
Figure 2A:
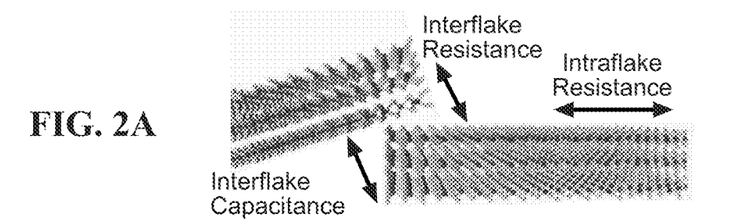
FIG. 2A is a schematic of flake interactions including interflake resistance, intraflake resistances, and interflake capacitance and example full frequency sweep data collection.
Figure 2B:
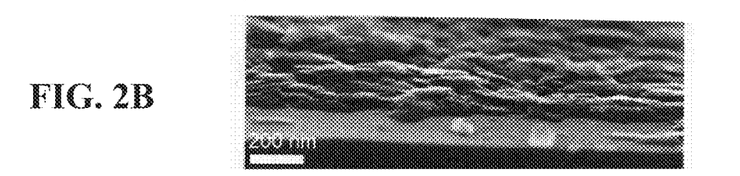
FIG. 2B is a cross-sectional SEM of aligned nanoflake film.
Figure 2C:
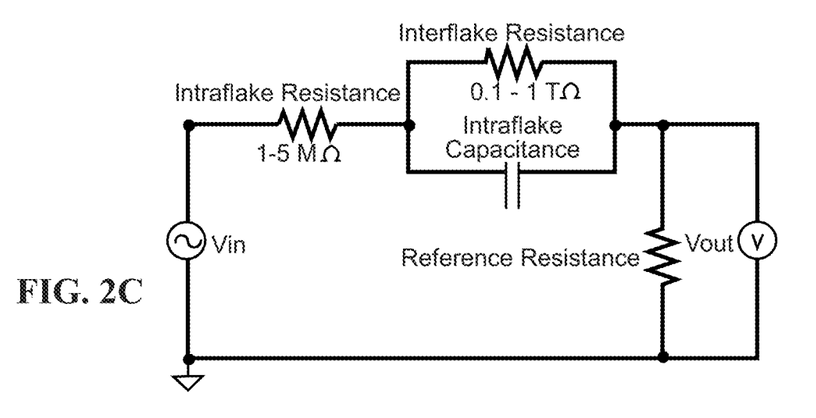
FIG. 2C is a schematic of an example circuit diagram for fitting the resistance and capacitive elements in an impedance nanoflake sensor
Figure 2D:
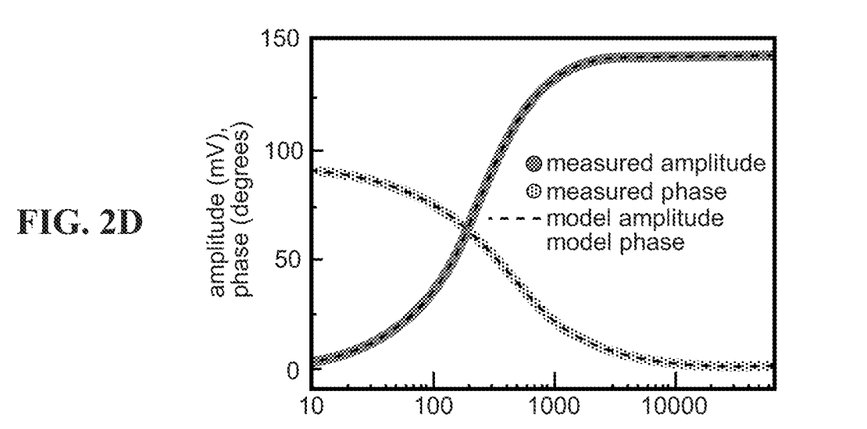
FIG. 2D is an example frequency response with measured amplitude and phase and modeled amplitude and phase
Figure 3A:
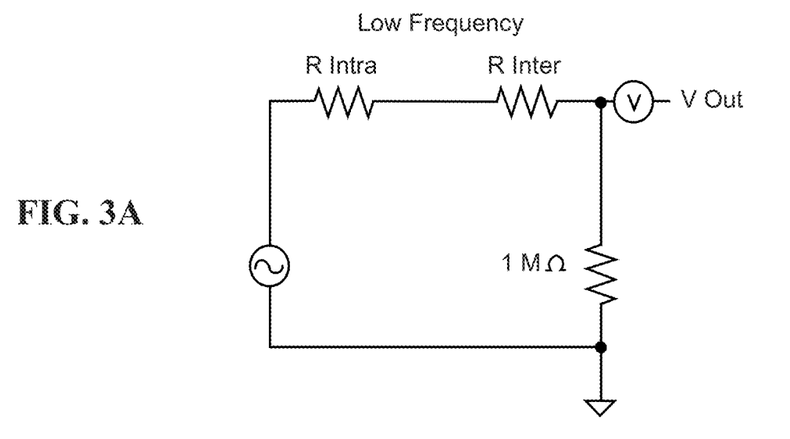
FIG. 3A is a schematic of a domain of a frequency simplification for the circuit model.
Figure 3B:
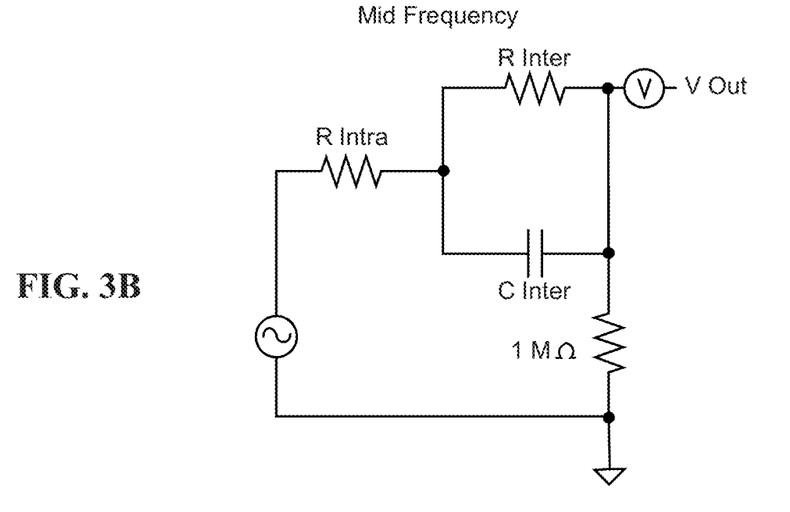
FIG. 3B is a schematic of a domain of a frequency simplification for the circuit model.
Figure 3C:
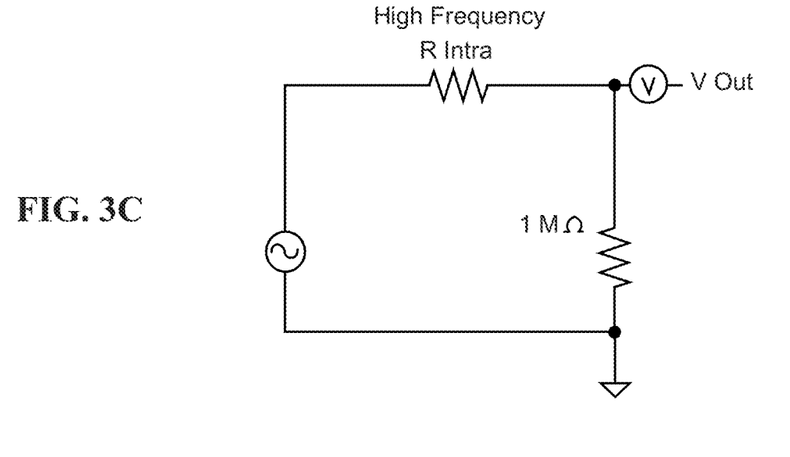
FIG. 3C is a schematic of a domain of a frequency simplification for the circuit model.
Figure 4:
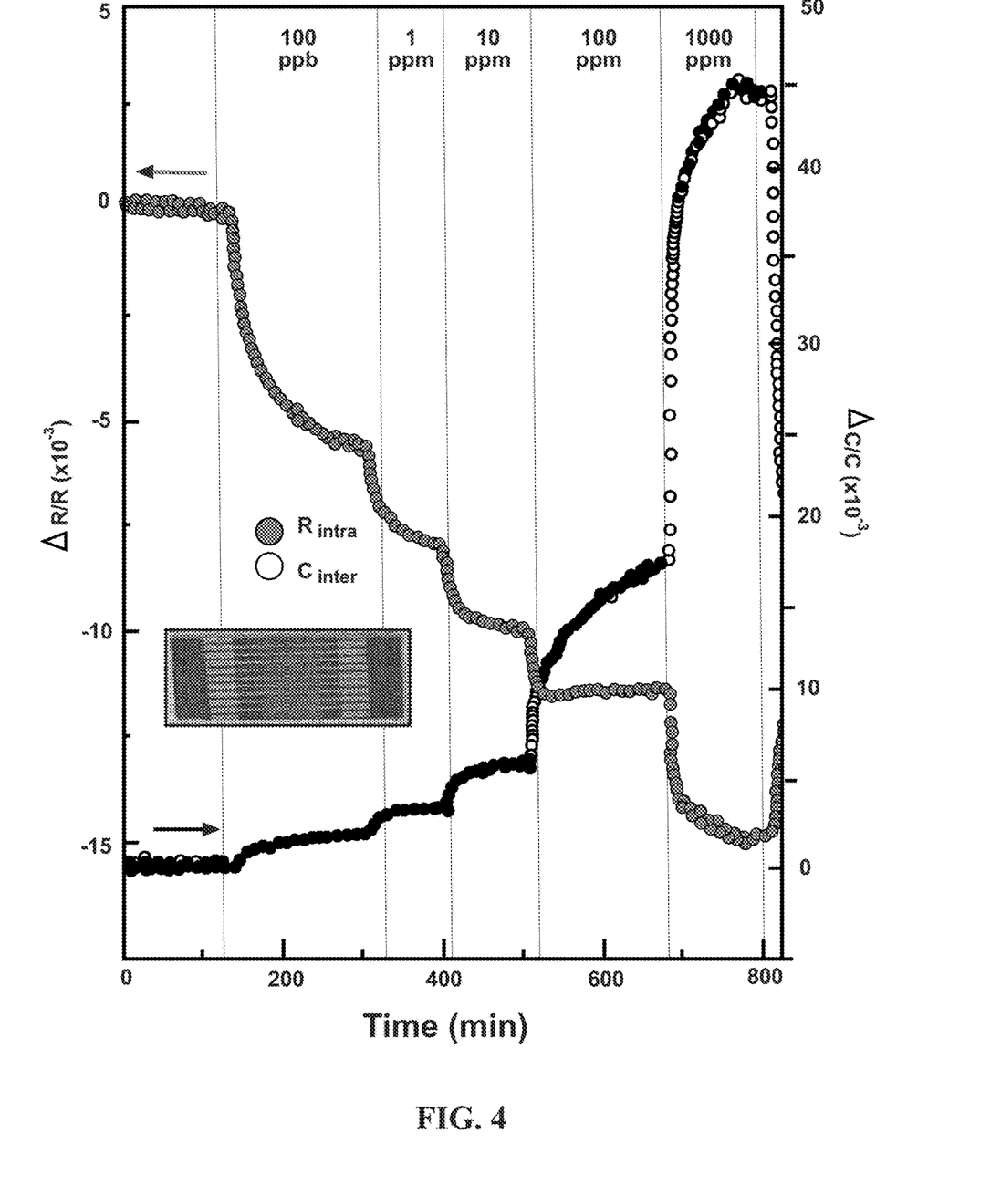
FIG. 4 is a sensor test depicting resistance and capacitance response at various $NO_2$ concentrations with inset image of flow coated $MoS_2$ 9-channel sensor device
Figure 5:
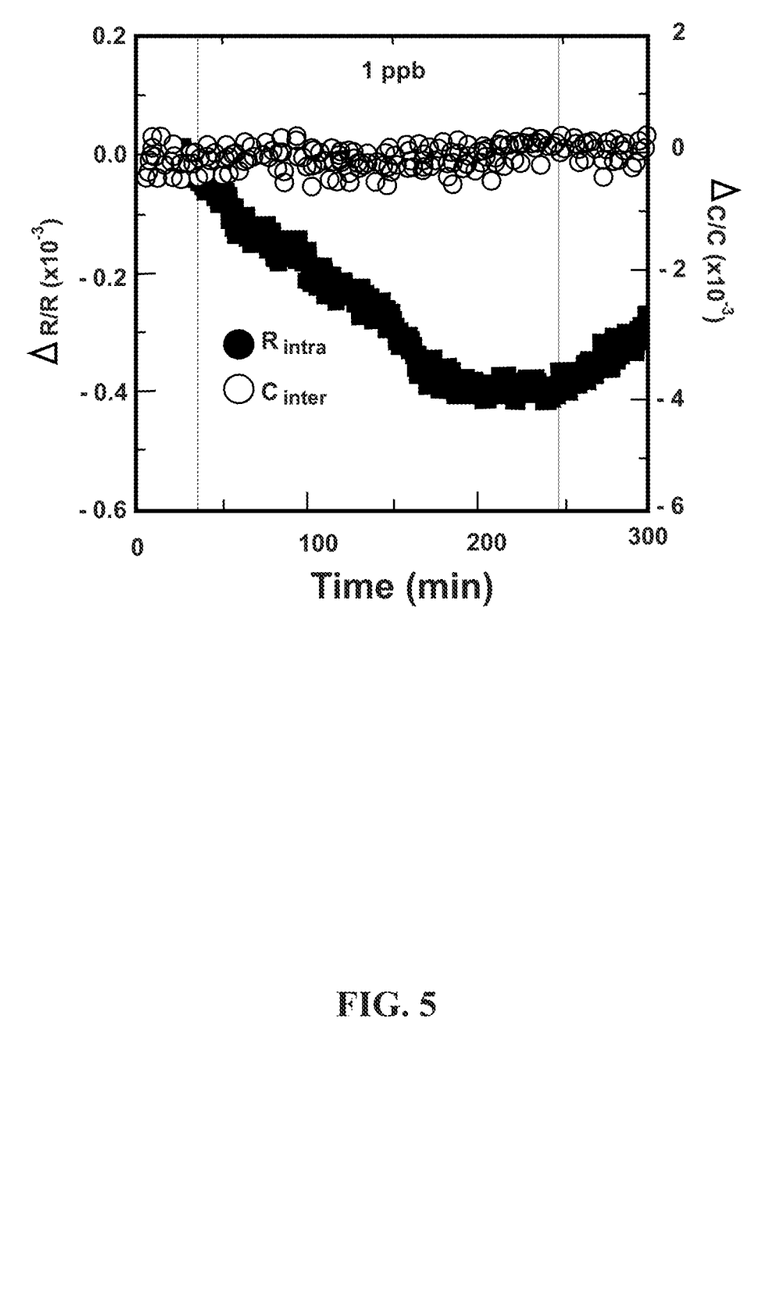
FIG. 5 is a 1 ppb sensor response from the real-time impedance nanoflake sensor depicting both capacitance and resistance varying over time under exposure to $NO_2$
Figure 6:
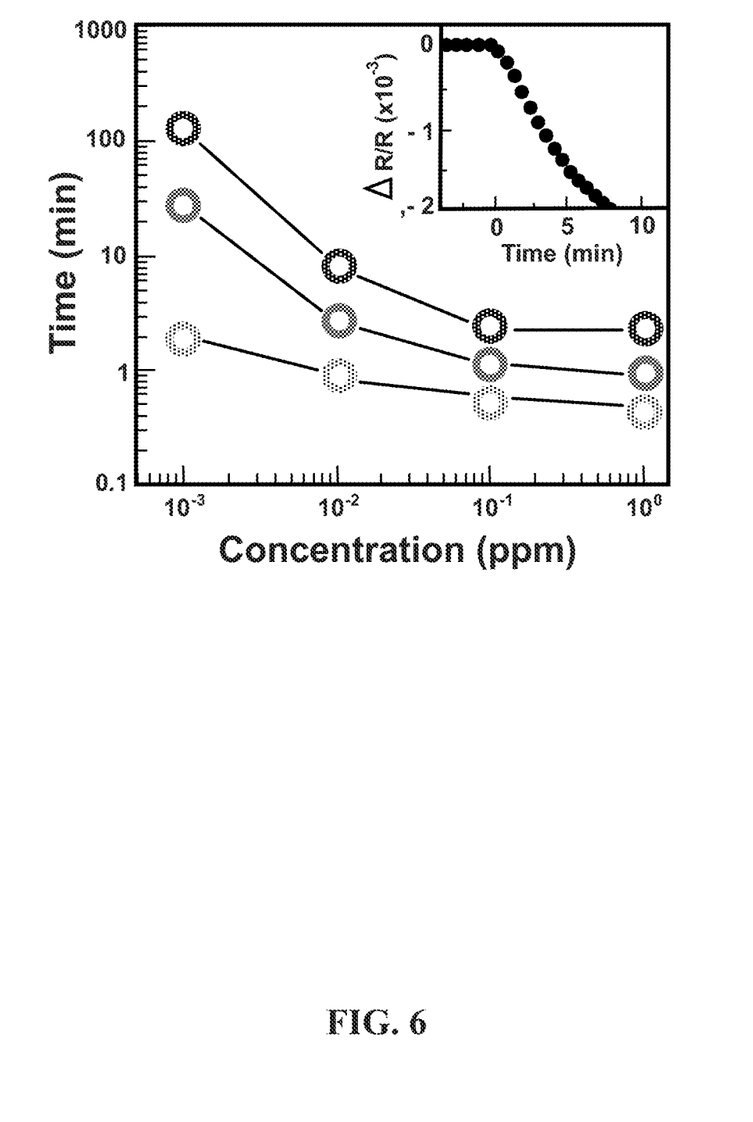
FIG. 6 is a concentration-dependent noise threshold with inset of initial sensor "trigger" to trip an alarm
Figure 7A:
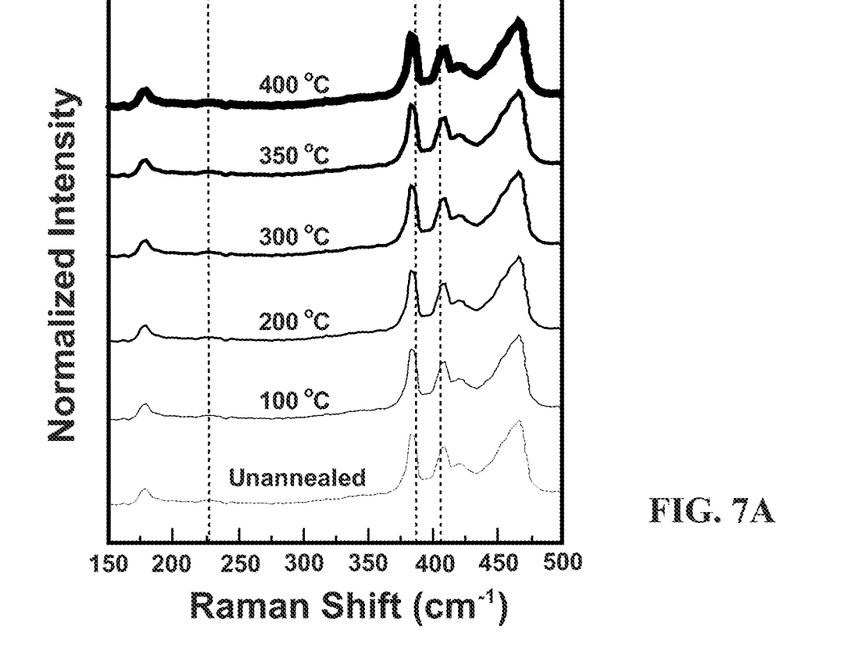
FIG. 7A depicts resonant 633 nm Raman spectroscopy of the $MoS_2$ nanoflake film at various annealing temperatures
Figure 7B:
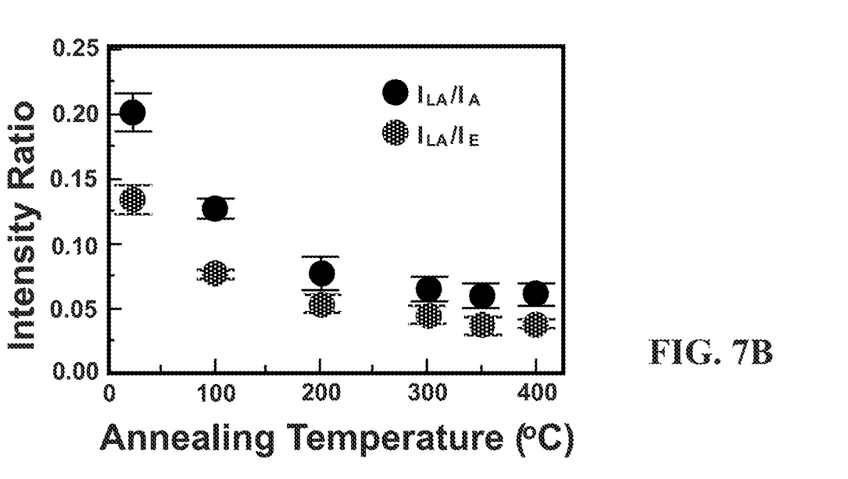
FIG. 7B depicts defect densities as a function of annealing temperature based on the ratio of the LA mode intensity to the $A_{1g}$ and $E_{2g}$ modes in resonant Raman of $MoS_2$ nanoflake films
Figure 7C:
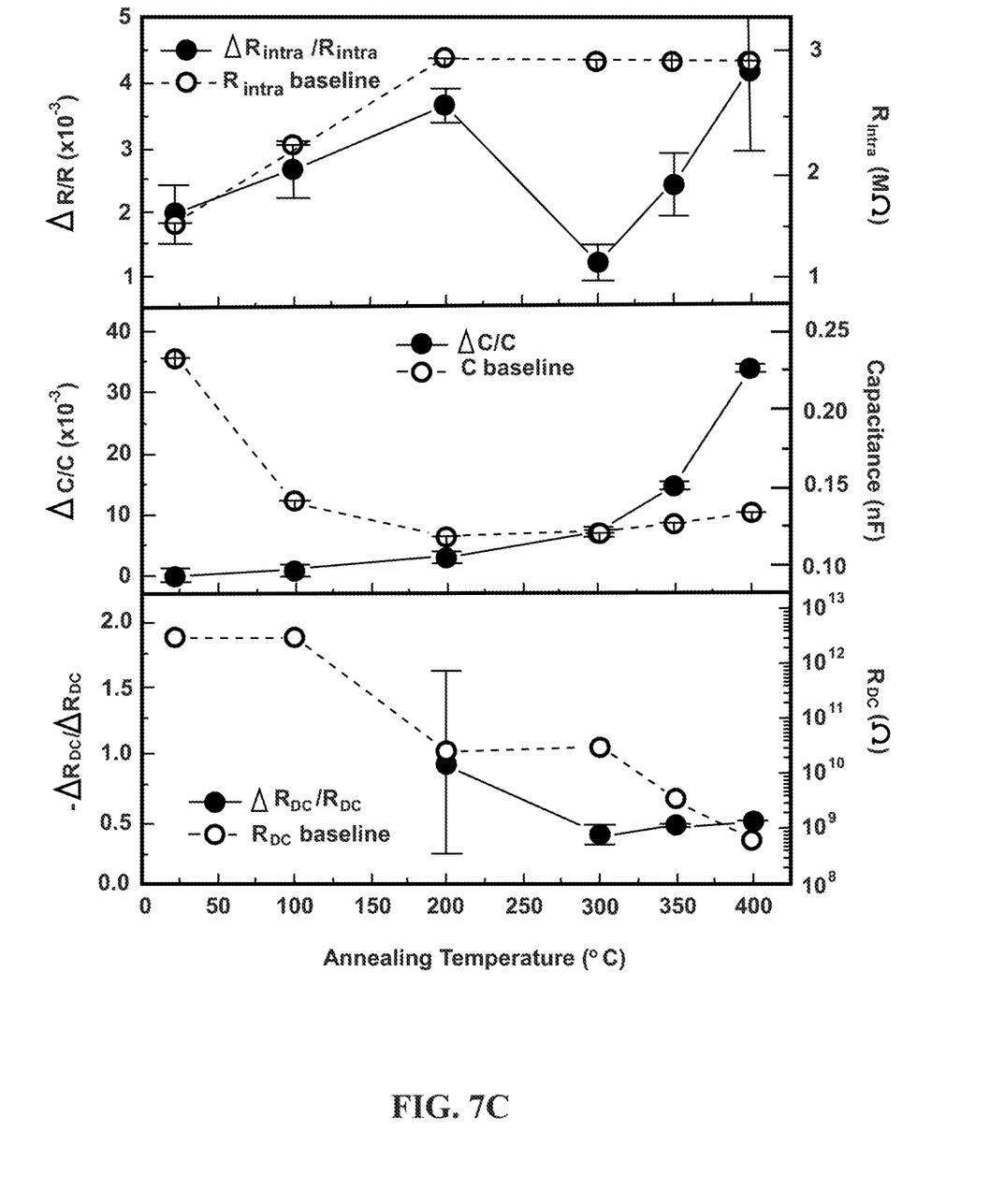
FIG. 7C is a representation of sensor results under 1 ppm $NO_2$ for all circuit elements at different annealing conditions
Figure 8A:
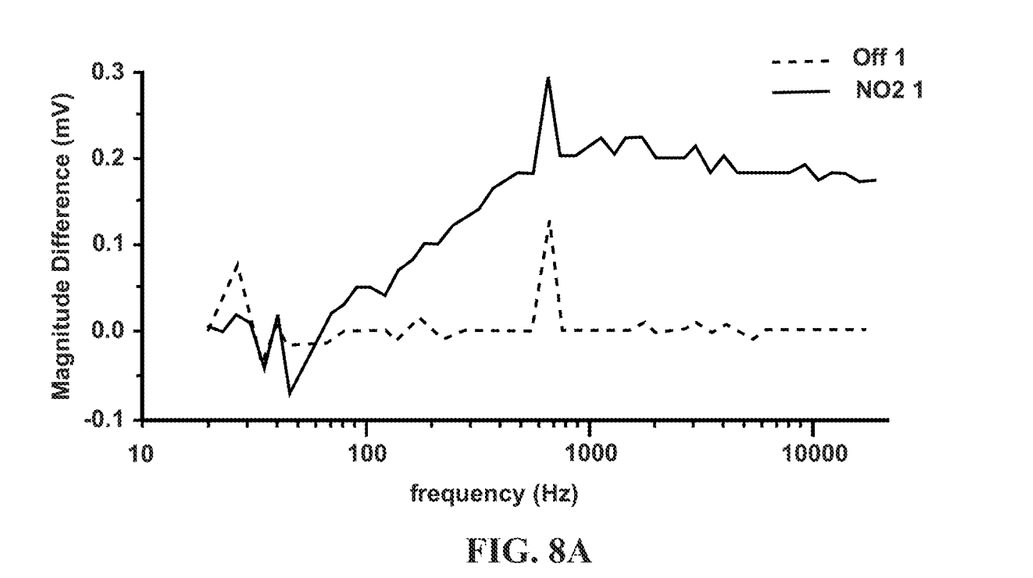
FIG. 8A is a portion of a sensor result with a single frequency that when viewed in conjunction with FIGS. 8B through 8E provides a view of a sensor result with a single frequency.
Figure 8B:
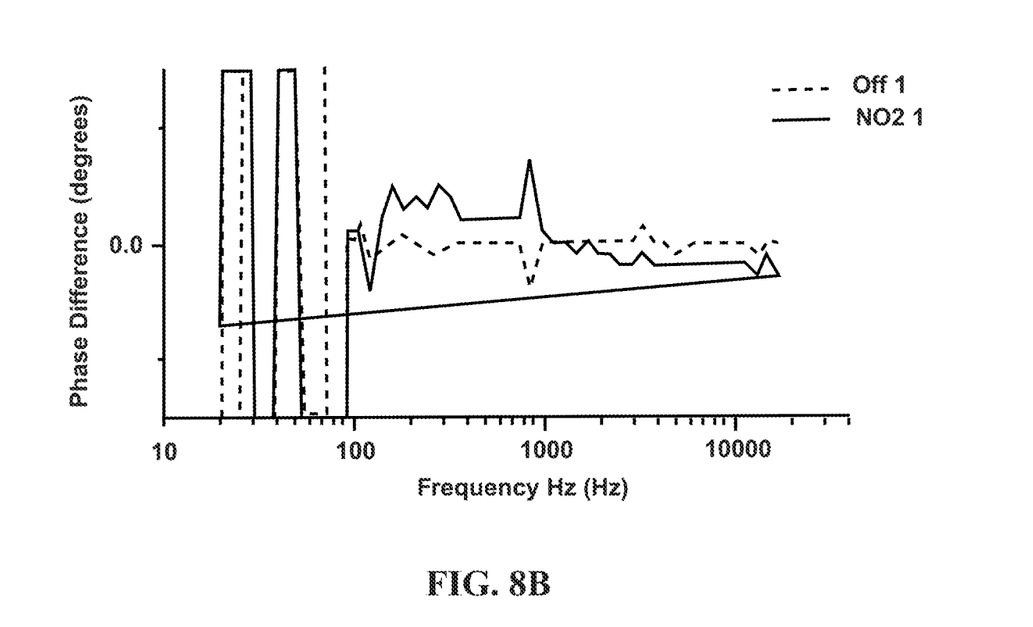
FIG. 8B is a sensor result with a single frequency that when viewed in conjunction with FIGS. 8A and 8C through 8E provides a view of a sensor result with a single frequency.
Figure 8C:
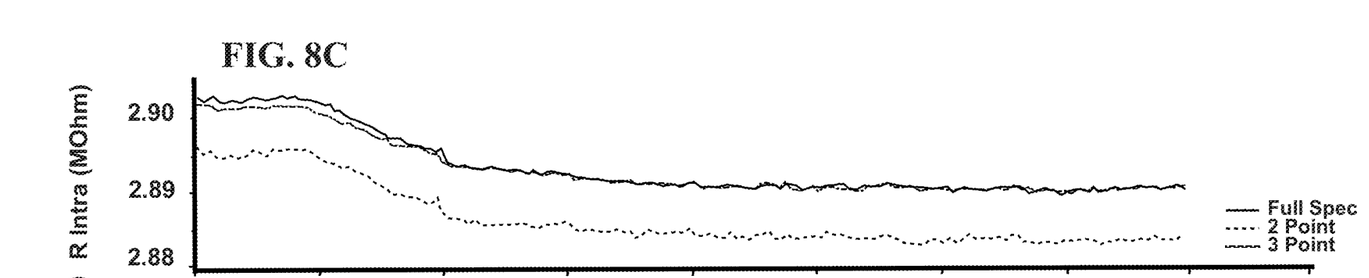
FIG. 8C is a sensor result with a single frequency that when viewed in conjunction with FIGS. 8A, 8B, 8D and 8E provides a view of a sensor result with a single frequency.
Figure 8D:
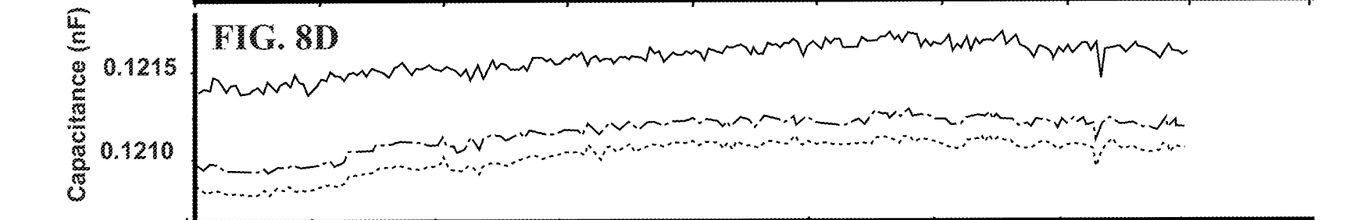
FIG. 8D is a sensor result with a single frequency that when viewed in conjunction with FIGS. 8A through 8C and 8E provides a view of a sensor result with a single frequency.
Figure 8E:
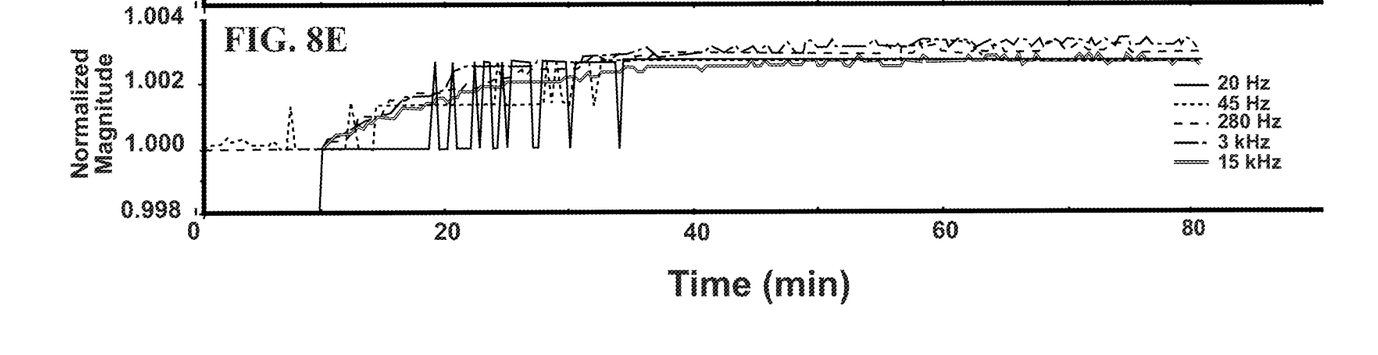
FIG. 8E is a sensor result with a single frequency that when viewed in conjunction with FIGS. 8A through 8D provides a view of a sensor result with a single frequency.

Example 1: Thin film nanoflake $MoS_2$ sensor on glass substrate. Few-layer MoS2 nanoflakes were exfoliated from bulk powders using the redox exfoliation process and dispersed in acetonitrile. The dispersions contain of few-layer $MoS_2$ flakes with an average flake diameter of approximately 100 nm and a thickness of 2-8 layers (FIG. 1A and FIG. 1B). The acetonitrile/$MoS_2$ dispersions were flow-coated onto an Si/SiO2 substrate with patterned Ti/Au contacts (10 nm Ti/50 nm Au) separated by a channel length of 100 µm. The flow coating was performed at a velocity of 0.22 mm/s to form cohesive thin films of that are approximately 80-100 nm in thickness. The flow-coated process induces mostly horizontally aligned flakes with crystallographic orientation on the 002 axis in between the contacts. The sensor device is then connected to a lockin amplifier to serve as both the ac current source and detector and the sensor is used to monitor exposure to $NO_2$ gas.

Example 2: WSe$_2$ nanoflake sensor on flexible kapton substrate and wearable platform. WSe$_2$ nanoflakes were drop casted to a thickness of 1000 nm onto a kapton sheet with interdigitated molybdenum contacts and a device spacing of 10 microns. The nanoflake device is connected to a potentiaostat that is integrated onto a wearable flexible electronics platform. The wearable system individually measures three different frequencies and applies an algorithm to measure humidity in the atmosphere with high precision.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and process, and illustrative examples shown and described. Accordingly, departures may be made from such details without departing from the scope of the general inventive concept.

What is claimed is:

1. A real-time impedance spectroscopy sensor system for detecting the concentration of a gas when said sensor system is exposed to said gas, said sensor system comprising:
 a) a substrate comprised of a host material, said host material having a top side and a bottom, said substrate further comprising:
  (i) a layer on the top side of said host material and/or on said bottom side of said host material, said layer comprising a plurality of transition metal dichalcogenide nanoflakes, said layer having a topside and a bottom side, wherein the nanoflakes have an impedance;
  (ii) a patterned electrical conductive material being disposed: on the topside of said layer, between said host material and said layer, or disposed on the topside of said layer and between said host material and said layer;
b) a power source;
c) an alternating current detector which provides alternating current readings as a measure of the impedance of the nanoflakes; and
d) a processor in electrical communication with said alternating current detector, said processor being configured for converting alternating current readings to break down the impedance into multiple, measurable resistance components, and process data in real time, wherein an electrical signal is generated by said sensor system due to gas exposure, and said electrical signal is compared to a baseline electrical signal to generate a value for said gas concentration in real time said patterned electrical conductive material and one or more of said plurality transition metal dichalcogenide nanoflakes being in electrical communication with said power source and said alternating current detector.

2. The sensor system of claim 1 wherein said power source is one of a variable AC frequency power source and a single AC frequency power source, and said alternating current detector is one of the following: a lockin amplifier, an ac voltmeter, an ammeter, a multimeter, a potentiostat, or an integrating circuit.

3. The sensor system of claim 2 wherein said power source is a single AC frequency power source that comprises a frequency converter, and said alternating current detector is selected from the group consisting of a lockin amplifier and a potentiostat.

4. The sensor system of claim 3 wherein said frequency converter is a transformer.

5. The sensor system of claim 1 wherein said power source is a variable AC frequency power source, and said alternating current detector is selected from the group consisting of a lockin amplifier, a function generator, variable frequency generator, or a potentiostat.

6. The sensor system of claim 1 wherein:
a) said host material is selected from the group consisting of silicon, silicon dioxide, sapphire, glass, a polymer and mixtures thereof;
b) said plurality transition metal dichalcogenide nanoflakes comprise $MoS_2$, $WS_2$, $MoSe_2$, $WSe_2$, $MoTe_2$, $WTe_2$ and mixtures thereof;
c) said patterned electrical conductive material comprises a material selected from the group consisting of poly(3,4-ethylenedioxythiophene), poly(3,4-ethylenedioxythiophene) polystyrene sulfonate, poly(pyrrole), polycarbazoles, polyindoles, polyazepines, Cr, Mo, Ti, Sc, Ni, V, Hf, W, Nb, Au, Ag, Cu, Pt and mixtures thereof.

7. The sensor system of claim 6 wherein:
a) said host material is a polymer selected from the group consisting of polyethylene naphthalate, polyimide, polycarbonate, and mixtures thereof; and
b) said patterned electrical conductive material comprises a metal selected from the group consisting of Cr, Mo, Ti, Sc, Ni, V, Hf, W, Nb, Au, Ag, Cu, and Pt and mixtures thereof.

8. The sensor system of claim 7 wherein said patterned electrical conductive material comprises at least one metal selected from the group consisting of Mo, Cr, Ti, Au and mixtures thereof.

9. The sensor system of claim 8 wherein said patterned electrical conductive material comprises one of the following:
(i) a coating of Mo,
(ii) a coating of Cr and a coating of Au over said coating of Cr; or
(ii) a coating of Ti and a coating of Au over said coating of Ti.

10. The sensor system of claim 1 wherein said plurality transition metal dichalcogenide nanoflakes have thickness of from 0.3 nm to 10,000 nm.

11. The sensor system of claim 10 wherein said plurality transition metal dichalcogenide nanoflakes have thickness of from 1 nm to 1000 nm.

12. The sensor system of claim 11 wherein said plurality transition metal dichalcogenide nanoflakes have thickness of from 3 nm to 100 nm.

13. A method of determining a gas concentration comprising:
exposing a sensor according to claim 1 to a gas;
b) taking an electrical signal that is generated by said sensor due to said gas exposure and comparing said electrical signal to a baseline electrical signal; and
c) generating a value for said gas concentration from said comparison of said electrical signal that is generated by said sensor due to said gas exposure and comparing said electrical signal to a baseline electrical signal.

14. The method of claim 13 wherein said gas is selected from the group consisting of organic gases, inorganic gases and mixtures thereof.

15. The method of claim 14 wherein said gas is selected from the group consisting of water, Ammonia, Benzyl chloride, Carbon monoxide, Carbon dioxide, Carbon disulfide, 1,4-dioxane, Hydrogen sulfide, Chlorine, Chlorine dioxide, Ethylene oxide, Formaldehyde, Hydrogen cyanide, Hydrogen sulfide, Methyl mercaptan, Methacrolein, Acrolein, Diisopropylamine, Tripropylamine, Napthanlene, Nitric oxide, Nitrogen dioxide, Oxygen, Phosphine, Sulfur dioxide, Isopropyl Alcohol, Methanol, Ethanol, Anile and Toluene and mixtures thereof.

16. The method of claim 13 wherein said gas concentration is from 100 ppt to 10,000 ppt.

17. The method of claim 16 wherein said gas concentration is from 1 ppb to 1000 ppm.

18. The sensor system of claim 1 which measures alternating current readings at multiple different frequencies.

19. The sensor system of claim 1 wherein:
the layer of nanoflakes has an interflake resistance, an intraflake resistance, and an interflake capacitance; and
the processor is configured to break down the impedance into multiple, measurable resistance and capacitor components, and create a circuit model of said resistance and capacitor components.

20. The sensor system of claim 1 further comprising e) a gas chamber, wherein said substrate is contained within said gas chamber.

* * * * *